(12) United States Patent
Meridew et al.

(10) Patent No.: US 8,500,819 B2
(45) Date of Patent: Aug. 6, 2013

(54) DRUG DELIVERY AND DIAGNOSTIC SYSTEM FOR ORTHOPEDIC IMPLANTS

(75) Inventors: Jason Meridew, Warsaw, IN (US); Mukesh Kumar, Warsaw, IN (US); Tayler E. Kreider, South Whitley, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 184 days.

(21) Appl. No.: 13/039,362

(22) Filed: Mar. 3, 2011

(65) Prior Publication Data

US 2011/0218644 A1  Sep. 8, 2011

Related U.S. Application Data

(60) Provisional application No. 61/311,096, filed on Mar. 5, 2010.

(51) Int. Cl.
*A61N 1/30*  (2006.01)
(52) U.S. Cl.
USPC .......................................... 623/20.35; 604/48

(58) Field of Classification Search
USPC ................. 623/20.35–20.36; 604/20, 48, 67
See application file for complete search history.

(56) References Cited

FOREIGN PATENT DOCUMENTS

| DE | 3704089 A1 | 8/1988 |
|---|---|---|
| GB | 2387115 A | 10/2003 |
| WO | WO-0048535 A1 | 8/2000 |
| WO | WO-2010025378 A2 | 3/2010 |

OTHER PUBLICATIONS

International Search Report mailed Jun. 15, 2011 in reference to Application No. GB1103663.9.

*Primary Examiner* — David Isabella
*Assistant Examiner* — Ann Schillinger
(74) *Attorney, Agent, or Firm* — Harness, Dickey

(57) ABSTRACT

A drug delivery and diagnostic system can include an orthopedic implant having an outer attachment surface. A conduit can be coupled to the outer attachment surface. The conduit can have an inlet and a plurality of perforations formed along a length thereof. The conduit can be adapted to pass fluid between the inlet and the perforations. A subcutaneous port can be fluidly coupled to the inlet and be adapted to communicate fluid through the inlet, along the conduit and out of the perforations around and along the outer attachment surface of the orthopedic implant.

11 Claims, 7 Drawing Sheets

DRUG DELIVERY AND DIAGNOSTIC SYSTEM FOR ORTHOPEDIC IMPLANTS

CROSS-REFERENCE TO RELATED APPLICATIONS

This application claims the benefit and priority of U.S. Provisional Application No. 61/311,096, filed Mar. 5, 2010. The entire disclosure of the above application is incorporated herein by reference.

FIELD

The present disclosure relates generally to orthopedic implants and more specifically to orthopedic implants having a drug delivery and diagnostic system.

BACKGROUND

This section provides background information related to the present disclosure which is not necessarily prior art.

Orthopedic implants have been used to partially or entirely replace bones and joints that may be damaged. In some examples however, infection on or near such orthopedic implants may take place after implantation of the orthopedic prosthesis. Moreover, the onset of infection on or near the orthopedic implant and tissue interface may be difficult to detect. Furthermore, the type of infecting agent may also be unknown. In some examples, once an infection is eventually detected, the recourse may be invasive and include extraction of the orthopedic implant and subsequent revision surgery. To address such concerns drug coated orthopedic implants have been developed. Drug coated orthopedic implants provide a coating on the implant to be effective against various bacteria and strain. Drug coated implants are generally most effective immediately after implantation of the orthopedic implant, such as when the eluting mechanism is activated upon contact with bodily fluid.

SUMMARY

This section provides a general summary of the disclosure, and is not a comprehensive disclosure of its full scope or all of its features.

A drug delivery and diagnostic system can include an orthopedic implant having an outer attachment surface. A conduit can be coupled to the outer attachment surface. The conduit can have an inlet and a plurality of perforations formed along a length thereof. The conduit can be adapted to pass fluid between the inlet and the perforations. A subcutaneous port can be fluidly coupled to the inlet and be adapted to communicate fluid through the inlet, along the conduit and out of the perforations around and along the outer attachment surface of the orthopedic implant.

According to additional features, the conduit can be spirally wrapped around the outer attachment surface. The conduit can be formed of biocompatible metal or polymer. The conduit can be attached to the outer attachment surface, such as by welding, brazing or gluing.

According to other features, a drug delivery system can comprise an orthopedic implant having a blind bore formed thereon and at least one passage that fluidly connects the blind bore with an outer surface of the orthopedic implant. An implant module can have a reservoir, a first radio frequency (RF) receiver, a fluid reservoir, and a valve that is selectively movable from a closed position wherein fluid is retained in the reservoir and an open position wherein the fluid is communicated out of the reservoir. The implant module can have an insertion end that is adapted to couple to the orthopedic implant at the blind bore. A handheld device having a second RF transmitter can communicate with the first RF receiver. The handheld device can be operable to send a signal from the second RF transmitter. The first RF receiver is operable to initiate movement of the valve to the open position upon receipt of the signal from the second RF transmitter.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. While a femoral stem is shown in FIGS. 1-6, other implants such as acetabular cups (FIG. 7), tibial trays (FIG. 8) and others may be used in conjunction with the disclosed system.

Figure 1:
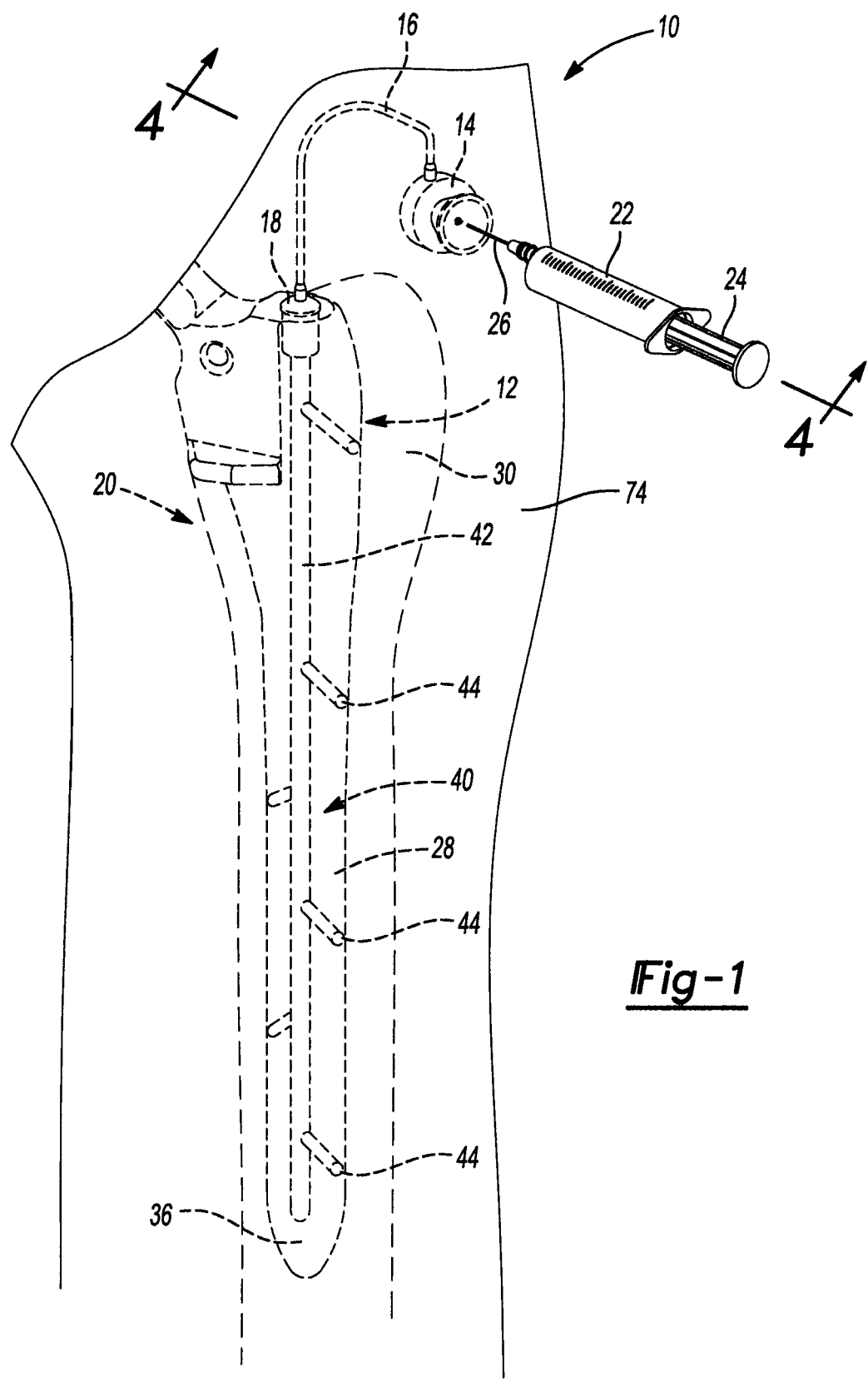
FIG. 1 is a perspective posterior view of a femoral stem implanted in an intramedullary canal of a right femur, the femoral stem incorporating the drug delivery and diagnostic system of the present teachings.
Figure 2:
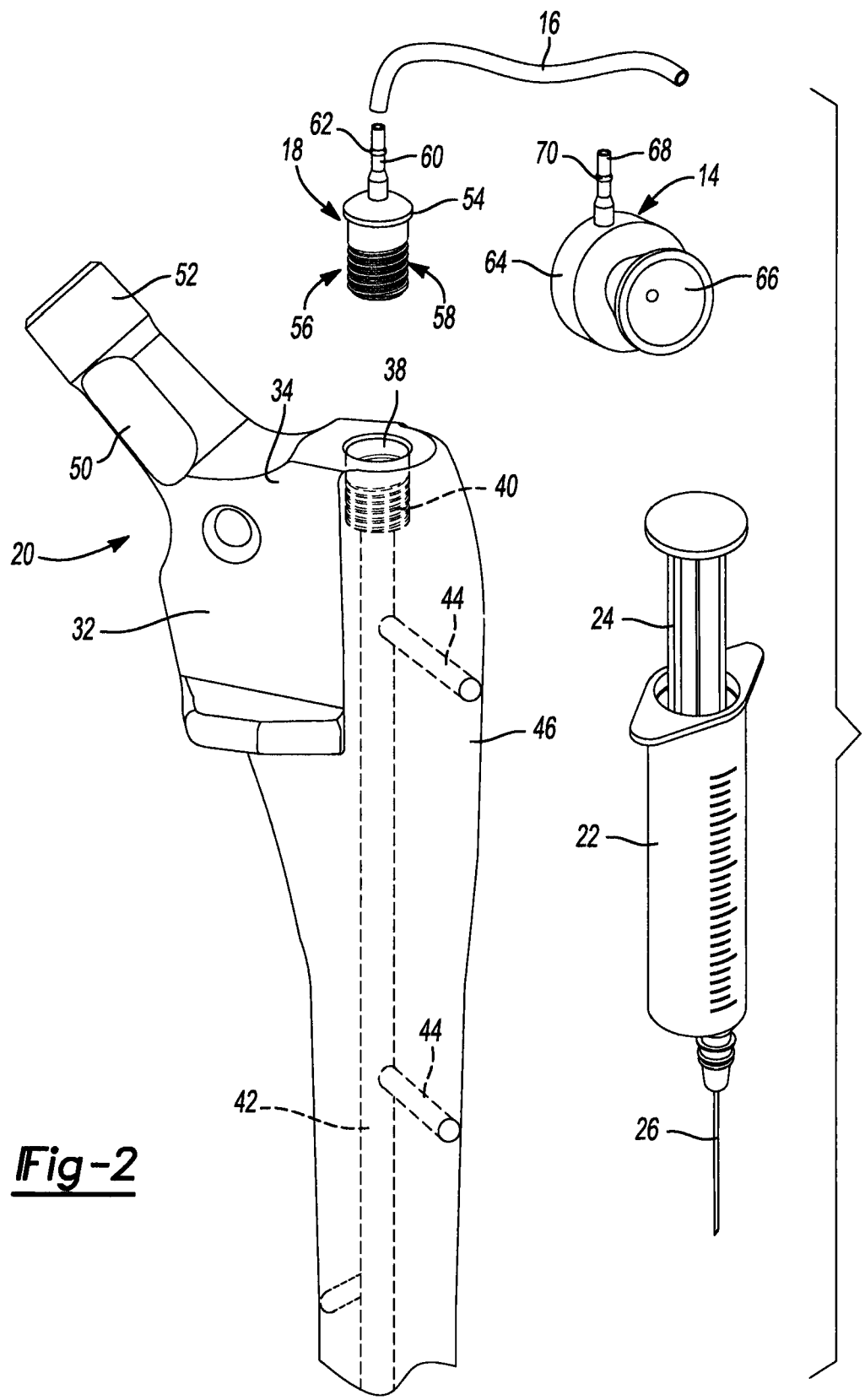
FIG. 2 is an exploded perspective view of the drug delivery and diagnostic system of FIG. 1.

With initial reference to FIGS. 1 and 2, a drug delivery and diagnostic system constructed in accordance to one example of the present teachings is shown and generally identified at reference numeral 10. The drug delivery and diagnostic system 10 can generally include an orthopedic implant 12, a subcutaneous port 14, a flexible catheter 16 and an adapter 18. As illustrated, the orthopedic implant is in the form of a femoral stem 20. As will be described in greater detail herein, a syringe 22 having a plunger 24 and a needle 26 can be used with the subcutaneous port 14, the flexible catheter 16 and the adapter 18 in a first sequence to assist in diagnosing an infection that may be present in the surrounding tissue adjacent the orthopedic implant 12. The syringe 22, plunger 24 and needle 26 can also be used with the subcutaneous port 14, the catheter 16 and adapter 18 in a second sequence to deliver drugs, such as antibiotics, cellular therapy including stem cells, such as from fat or bone marrow aspirate, autologous blood components or other flowable therapies to the surrounding tissue adjacent the orthopedic implant 12.

As shown in FIG. 1, the femoral stem 20 is shown implanted into an intramedullary canal 28 of a femur 30. As best shown in FIG. 2, the femoral stem 20 can generally comprise a body 32 having a proximal body portion 34 and a distal stem portion 36. A blind bore or inserter hole 38 can be formed on the proximal body portion 34. The inserter hole 38 can be tapered and have threads 40 formed around an inner diameter thereof. The inserter hole 38 can be used for coupling with an inserter tool (not shown) during insertion of the femoral stem 20 into the intramedullary canal of the femur 30. The femoral stem 20 can further include a fluid passage system 40 that can include a primary passage 42 that is fluidly coupled to the inserter hole 38 and to a series of secondary passages 44 defined within the implant 12. The secondary passages 44 can extend to an outer surface 46 of the femoral stem 20. By way of example, six secondary passages 44 are illustrated in the exemplary configuration of FIG. 1. However, it will be appreciated that additional or fewer secondary passages can be provided in the femoral stem 20 that fluidly connects the primary passage 42 with the outer surface 46. Furthermore, it will be appreciated that the secondary passages 44 can be formed at right angles or non-orthogonal angles with respect to the primary passage 42 and a long axis of the femur 30. The proximal body portion 34 can further comprise a neck 50 having a male taper 52. While not specifically shown, the male taper 52 can be operable to couple with a femoral head as is known in the art. The adapter 18 can generally comprise an adapter body 54 having a longitudinal tapered insertion end 56 that has adapter threads 58 formed around an outer surface. An adapter nipple 60 can extend on an opposite end of the adapter body 54. The adapter nipple 60 can include a rib 62 thereon.

The subcutaneous port 14 can generally comprise a port body 64 that has an artificial septum 66 arranged thereon. A subcutaneous port nipple 68 can extend from the body 64. A rib 70 can be formed around the subcutaneous port nipple 68. It will be appreciated that the subcutaneous port 14 can take other forms. The catheter 16 can be operable to be slidably advanced at opposite terminal ends onto the adapter nipple 60 and the subcutaneous port nipple 68, respectively. The catheter 16 can be coated with and/or made with antifouling (antibacterial) material.

In one example of assembling the adapter 18 to the femoral stem 20, the adapter threads 58 can be threadably advanced into the inserter hole 38 at the proximal body portion 34 of the femoral stem 20. In this regard, the adapter threads 58 threadably advance around the threads 40 provided in the inserter hole 38. Again, the ends of the catheter 16 can be slidably advanced into a secure relationship with the respective adapter nipple 60 and subcutaneous port nipple 68. It will be appreciated that the catheter 16 can comprise any length suitable for a particular patient that allows the subcutaneous port 14 to be implanted under skin 74 (FIGS. 1 and 4) at a convenient access area of the patient.

Figure 3:
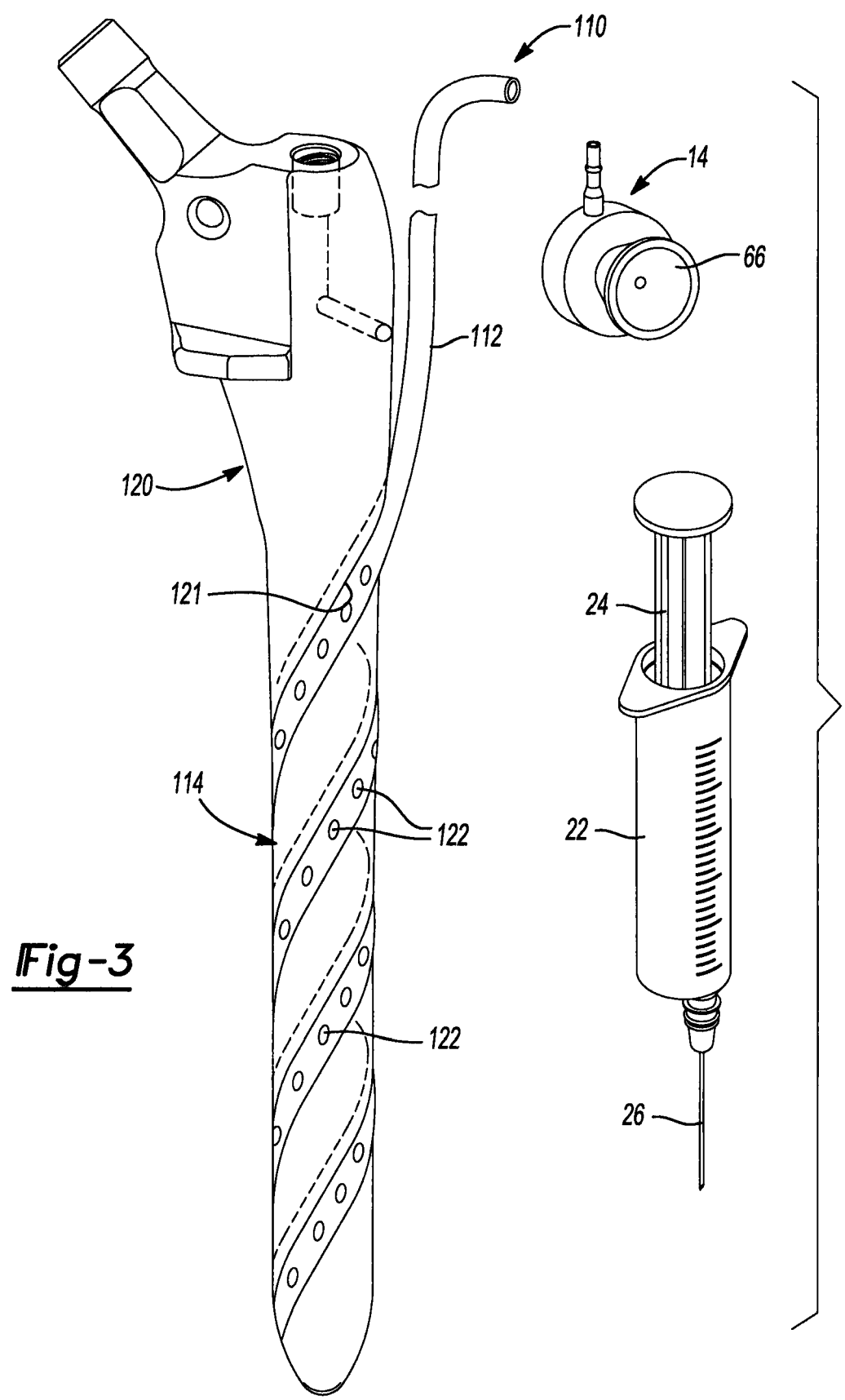
FIG. 3 is a perspective view of a drug delivery and diagnostic system according to additional features of the present teachings.

Turning now to FIG. 3, a drug delivery and diagnostic system 110 constructed in accordance to additional features of the present teachings is shown. In general, the drug delivery and diagnostic system 110 can include a flexible pipe or conduit 112 that is wrapped around a groove 121 formed in an outer attachment surface 114 of a femoral stem 120. It is appreciated that the groove 121 may extend further superiorly up the neck of the femoral stem 120. The groove 121 can have a depth such that the conduit 112 does not extend past the outer attachment surface. The conduit 112 can generally comprise a plurality of perforations 122 along its length. In other examples, the conduit 112 can include one or a series of linear or substantially linear pipes that branch out and extend along the outer attachment surface 114. In one example, the conduit 112 can be formed of biocompatible metallic material and can be attached to the outer attachment surface 114 (or more specifically into the groove 121), such as by a welding or brazing technique. The conduit can alternatively be formed of a polymer and attached to the groove 121 by an adhesive such as glue. The drug delivery and diagnostic system 110 can cooperate with the subcutaneous port 14 and the syringe 12 to deliver therapy and/or extract bodily fluid during a diagnostic test as discussed with respect to the drug delivery and diagnostic system 10 herein.

Figure 4:
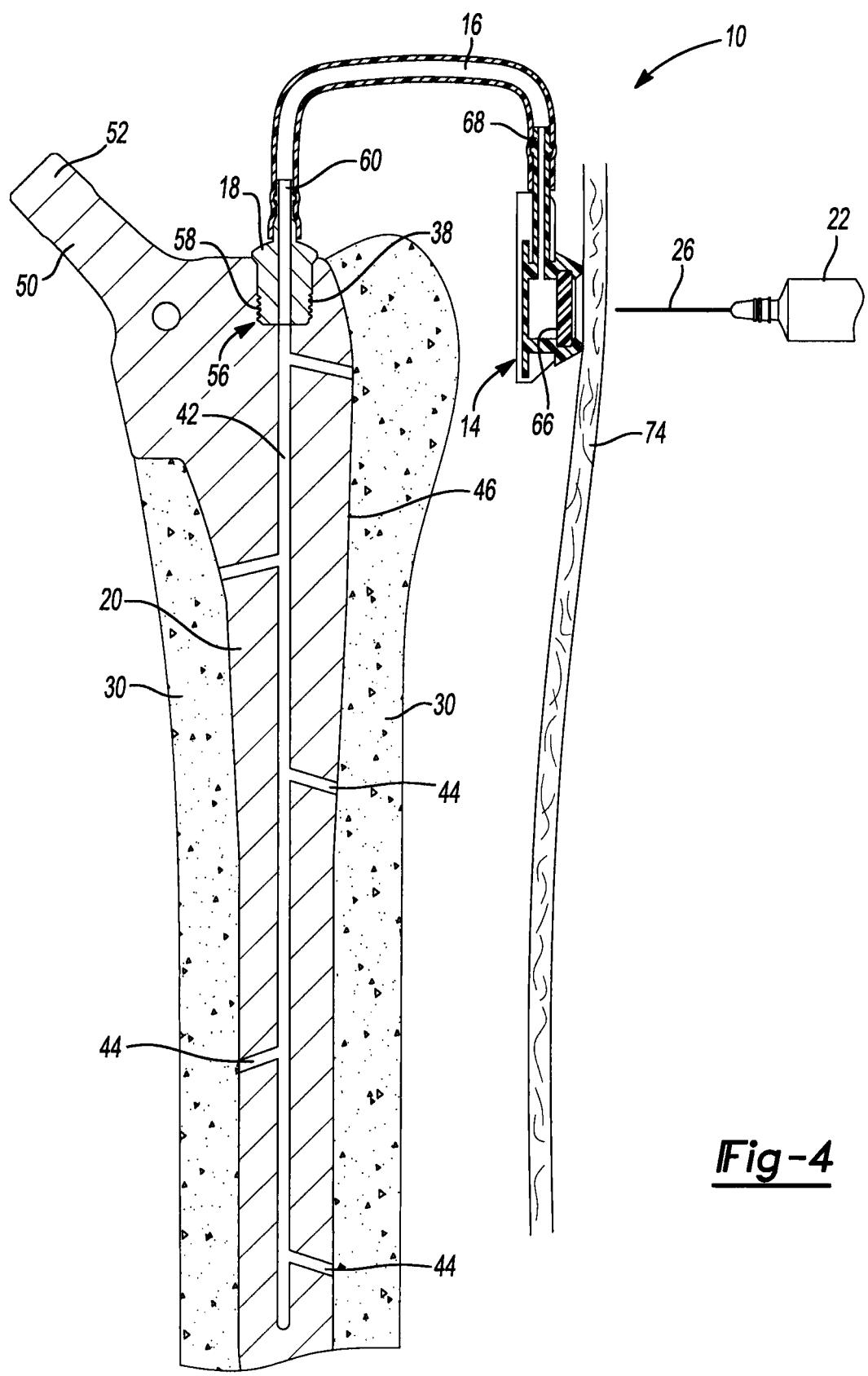
FIG. 4 is a sectional view of the drug delivery and diagnostic system taken along lines 4-4 of FIG. 1 and shown prior to insertion of a needle into a subcutaneous port implanted below the skin of a patient.
Figure 5:
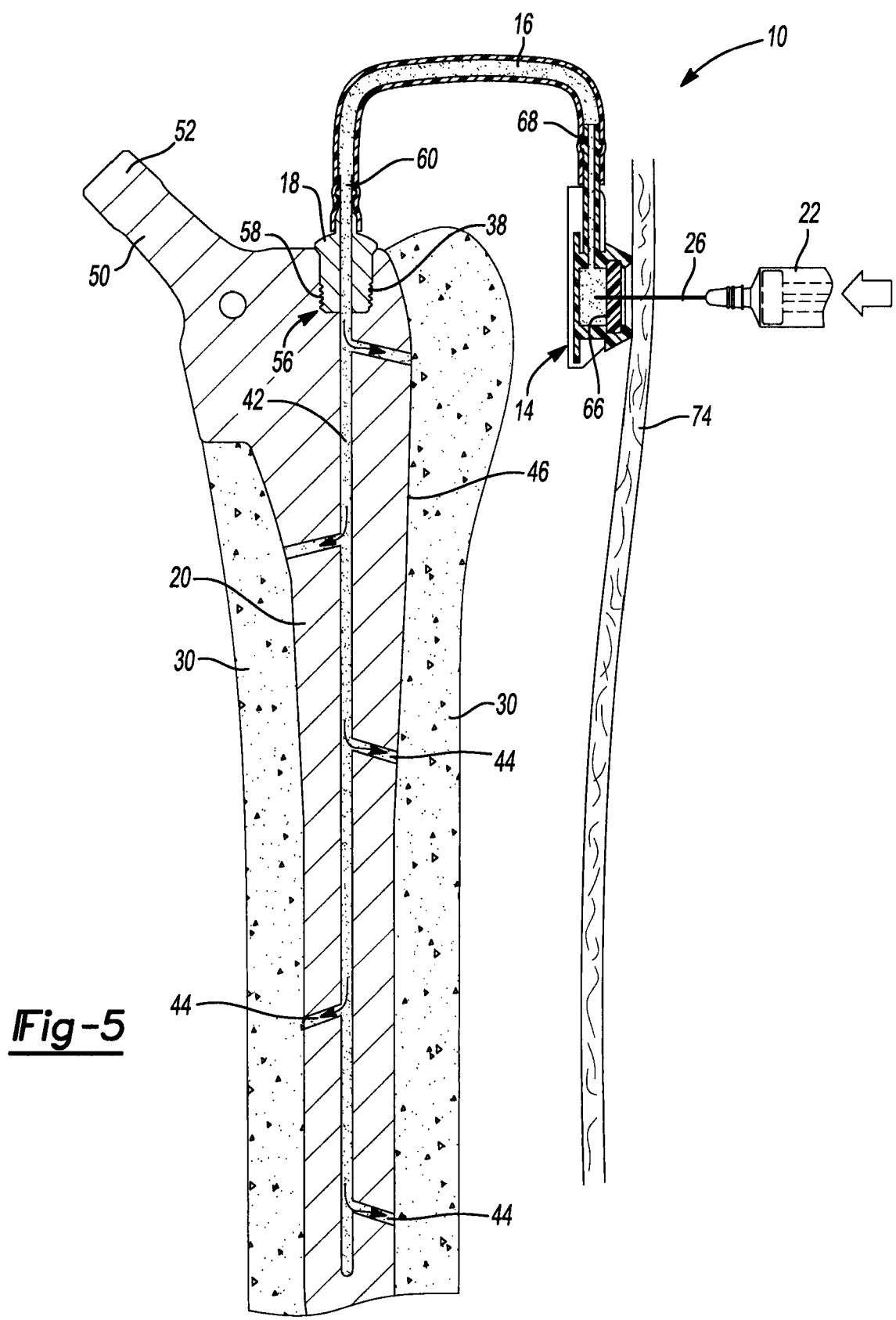
FIG. 5 is a cross-sectional view of the drug delivery and diagnostic system of FIG. 4 and shown subsequent to delivery of fluid through respective passages formed in the femoral stem.

With reference now to FIGS. 4 and 5, a first method of using the drug delivery and diagnostic system 10 will be described. In the first method according to the present teachings, the drug delivery and diagnostic system 10 will be used to diagnose potential bacteria that may be present at an interface between the femoral stem 20 and the femur 30. At the outset, the surgeon can draw fluid from a container (not shown), such as saline into the syringe 22. Next, the surgeon can pierce the skin 74 of the patient and pierce the artificial septum 66 of the subcutaneous port 14. The plunger 24 can then be depressed, such that the saline communicates through the catheter 16 and through the adapter 18, through the primary and secondary passages 42 and 44 and ultimately into the surrounding tissue around the outer surface 46 of the femoral stem 20. At this point, the saline can act to dislodge bacteria and therefore mix with any potential bacteria. Next, a surgeon can retract the plunger 24 and aspirate the saline and the bodily fluid that surrounds the outer surface 46. The resultant mixture can then be cultured to determine if any bacteria (and specific type etc.) is present in the suspected infection site around the outer surface 46 of the femoral stem 20.

With specific reference now to FIG. 5, the drug delivery and diagnostic system 10 will be described in accordance to a second method where the syringe 22 can be used to delivery a therapy, such as drugs, cellular therapy and/or autologous blood components to the implant-tissue interface. Again, it will be appreciated that with the first or second method, the drug delivery and diagnostic system can be used at any time, such as immediately after implantation of the femoral stem 20 or at any time, such as a year or many years after implantation of the femoral stem 20. Once the surgeon has determined what flowable agent is desired to be communicated to the interface of the femoral stem 20 and femur 30, the surgeon can pierce the artificial septum 66 of the subcutaneous port 14 with the needle 26 and depress the plunger 24 to deliver the flowable agent through the catheter 16, through the adapter 18 and through the respective primary and secondary passages 42 and 44. This enables the drug to be delivered around a perimeter of implant 12 at the infection site. The system can therefore be more efficient and effective compared to medications taken orally or intravenously.

Figure 6:
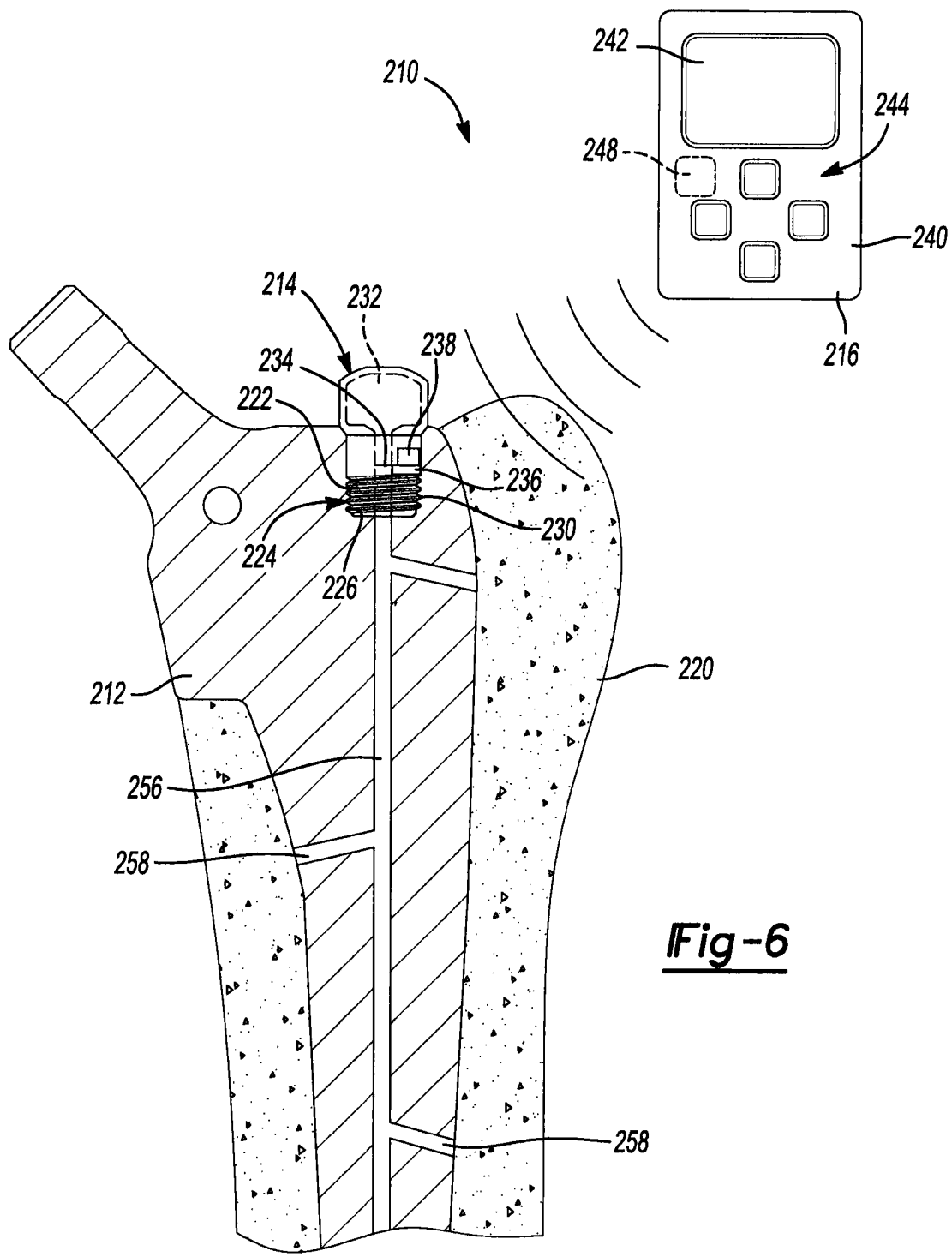
FIG. 6 is an exploded view of a drug delivery system constructed in accordance to additional features of the present disclosure and including a remote handheld device.

With specific reference now to FIG. 6, a drug delivery system 210 constructed in accordance to additional features of the present teachings is shown. The drug delivery system 210 can generally include an orthopedic implant 212, an implant module 214 and a handheld device 216. Unless otherwise described herein, the orthopedic prosthesis 212 can be constructed similarly to the femoral stem 20 described in detail above. In general, the drug delivery system 210 is operable to remotely communicate with the implant module 214, such that flowable material, such as antibiotics housed in the implant module 214 can be delivered to the tissue interface between the orthopedic prosthesis 212 and the femur 220.

The implant module 214 can generally comprise an insertion end 222 having module threads 224. As with the adapter 18 described above, the module threads 224 can be configured to threadably mate with blind bore threads 226 provided on an inserter hole 230 of the orthopedic implant 212. The implant module 214 can further comprise a reservoir 232, a valve 234, an actuator 236 and a first radio frequency (RF) receiver 238. The handheld device 216 can generally comprise a housing 240 having a display 242, an interface panel 244 and a second RF transmitter 248.

One exemplary method of using the drug delivery system 210 will now be described. Once a surgeon, medical professional or patient has determined that antibiotics (or other flowable material described herein) is desired to be communicated to a tissue interface between the orthopedic prosthesis 212 and the femur 220, a signal can be communicated from the second RF transmitter 248 of the handheld device 216. Upon receipt of the signal sent from the second RF transmitter 248, the first RF receiver 238 can communicate with the actuator 236 to cause the actuator 236 to open the valve 234 from a closed position to an open position wherein antibiotics (or other fluid) can be communicated through the primary passage 256 and secondary passages 258 and to the tissue interface between the orthopedic prosthesis 212 and the femur 220.

Figure 7:
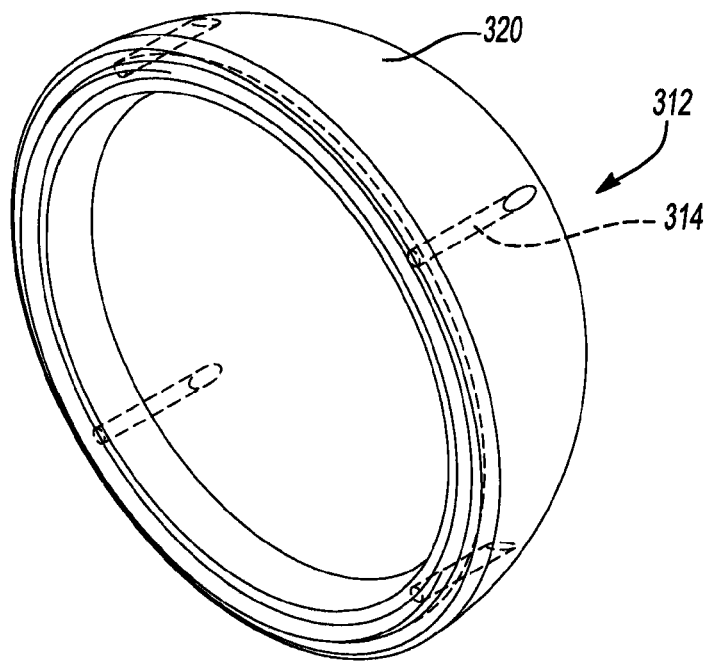
FIG. 7 is a perspective view of an acetabular cup incorporating a drug delivery and diagnostic system according to additional features of the present teachings.

Turning now to FIG. 7, an orthopedic implant 312 that incorporates respective passages 314 is shown. As illustrated, the orthopedic prosthesis 312 is in the form of an acetabular cup 320. The orthopedic prosthesis 312 can be used with other components described herein, such as the subcutaneous port 14, the catheter 16 and the syringe 22. As can be appreciated, the acetabular cup 320 can be used in a similar fashion as the femoral stem 20 described above. In this way, the fluid passages 314 can be used to assist in diagnosing a potential infection and/or to deliver antibiotic or other flowable material to an outer surface of the acetabular cup 320.

Figure 8:
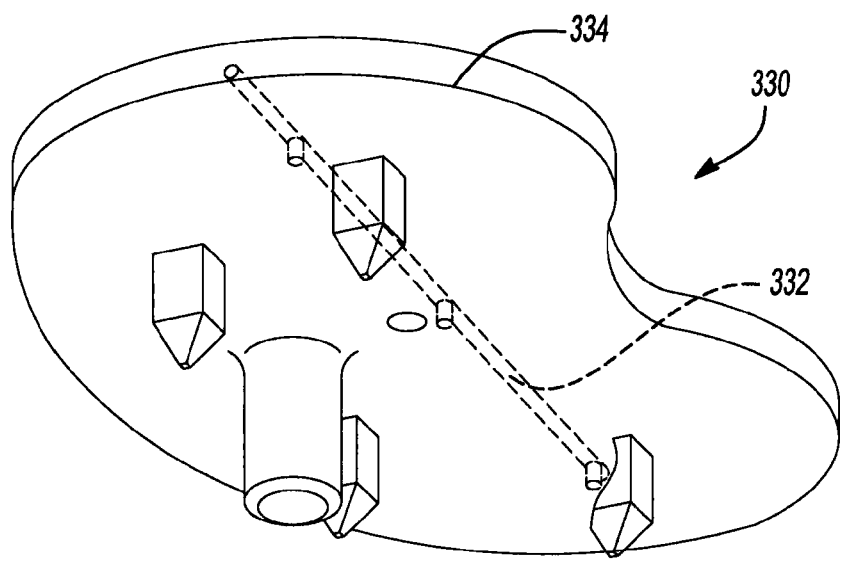
FIG. 8 is a perspective view of a tibial tray incorporating a drug delivery and diagnostic system according to other features of the present disclosure.

As shown in FIG. 8, an orthopedic prosthesis 330 is shown that incorporates fluid passage 332. The orthopedic prosthesis 330 is in the form of a tibial tray 334. As can be appreciated, the orthopedic prosthesis 330 can be used with other components described herein, such as the subcutaneous port 14, the catheter 16, and the syringe 22. In this regard, the fluid passage 332 can be used to assist in diagnosing a potential infection around the tibial tray 34, such as by one of the methods described above. Similarly, the fluid passage 332 can be used to deliver antibiotics or other flowable material to an outer surface of the tibial tray.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A drug delivery and diagnostic system comprising:
    an orthopedic implant having a blind bore formed thereon and at least one passage that fluidly connects the blind bore with an outer surface of the orthopedic implant;
    an implant module having a first radio frequency (RF) receiver, a fluid reservoir, and a valve that is selectively movable from a closed position wherein fluid is retained in the fluid reservoir and an open position wherein the fluid is communicated out of the fluid reservoir, the implant module having an insertion end adapted to couple to the orthopedic implant at the blind bore;
    a control device having a second RF transmitter that communicates with the first RF receiver wherein the control device is operable to send a signal from the second RF transmitter and wherein the first RF receiver is operable to initiate movement of the valve to the open position upon receipt of the signal from the second RF transmitter.

2. The drug delivery and diagnostic system of claim 1, further comprising an actuator that moves the valve from the closed to the open position.

3. The drug delivery and diagnostic system of claim 1 wherein the fluid comprises at least one of antibiotics, autologous biologics and cellular therapy.

4. The drug delivery and diagnostic system of claim 1 wherein the orthopedic implant comprises a femoral component.

5. The drug delivery and diagnostic system of claim 4 wherein the blind bore is operable to receive an insertion tool operable to assist in implanting the femoral component.

6. The drug delivery and diagnostic system of claim 1, wherein the control device further has at least one of a display or an interface panel.

7. The drug delivery and diagnostic system of claim 1, wherein the at least one passage includes at least a primary passage fluidly coupled to the blind bore and a secondary passage fluidly coupled to the primary passage.

8. The drug delivery and diagnostic system of claim 7, wherein the secondary passage extends at an angle to the primary passage.

9. The drug delivery and diagnostic system of claim 8, wherein the secondary passage extends to an outer surface of the femoral component.

10. The drug delivery and diagnostic system of claim 9, wherein the secondary passage includes a plurality of secondary passages, wherein each secondary passage of the plurality of secondary passages extends to the outer surface of the femoral component.

11. The drug delivery and diagnostic system of claim 1, wherein the blind bore includes internal threads and the implant module includes external threads, wherein the internal threads and the external threads are configured to interact to couple the implant module to the orthopedic implant at the blind bore.

* * * * *